United States Patent
Shewmake et al.

(10) Patent No.: US 6,812,033 B2
(45) Date of Patent: Nov. 2, 2004

(54) METHOD FOR IDENTIFYING RISK CARDIOVASCULAR DISEASE PATIENTS

(75) Inventors: David Shewmake, San Francisco, CA (US); Frank Ruderman, San Carlos, CA (US); Christopher Boggess, San Francisco, CA (US)

(73) Assignee: Berkeley HeartLab, Inc., San Mateo, CA (US)

( * ) Notice: Subject to any disclaimer, the term of this patent is extended or adjusted under 35 U.S.C. 154(b) by 0 days.

(21) Appl. No.: 10/122,081

(22) Filed: Apr. 12, 2002

(65) Prior Publication Data

US 2003/0194812 A1 Oct. 16, 2003

(51) Int. Cl.⁷ .............................................. G01N 33/92
(52) U.S. Cl. ......................... 436/71; 436/516; 204/456
(58) Field of Search ........................... 436/71, 53, 516; 240/456

(56) References Cited

U.S. PATENT DOCUMENTS 5,925,229 A * 7/1999 Krauss et al. ............... 204/606
6,576,471 B2 * 6/2003 Otvos ......................... 436/71

OTHER PUBLICATIONS

Superko "Lipoprotein Subclasses and atherosclerosis", Front. Biosci., Mar. 1, 2001, D355–365.*
Rainwater "Electrophoretic separation of LDL and HDL subclasses", Methods Mol. Biol., 1998, v. 110, pp. 137–151 (Abstract).*

* cited by examiner

Primary Examiner—Yelena G. Gakh
(74) Attorney, Agent, or Firm—McDonnell Boehnen Hulbert & Berghoff

(57) ABSTRACT

The invention provides a method for identifying patients with normal NCEP lipid levels who are in need of treatment for cardiovascular disease comprising measuring one or more LDL or HDL particle subclass levels and identifying abnormal LDL or HDL subclass levels.

9 Claims, No Drawings

METHOD FOR IDENTIFYING RISK CARDIOVASCULAR DISEASE PATIENTS

FIELD OF THE INVENTION

This invention is in the field of cardiovascular healthcare management and patient treatment.

BACKGROUND OF THE INVENTION

According to the National Cholesterol Education Program (NCEP) guidelines, low density lipoprotein (LDL) cholesterol goals and criteria for Therapeutic Lifestyle Changes and Drug Therapy in different risk categories are as follows:

| Risk Category | LDL Goal | LDL level to initiate Therapeutic Lifestyle Changes | LDL level to consider Drug Therapy |
| --- | --- | --- | --- |
| CHD or CHD Risk Equivalents | <100 mg/dL | 100 mg/dL | 130 mg/dL (10 yr risk 10–20%) 160 mg/dL (10-yr risk < 10%) |
| 2+ Risk Factors | <130 mg/dL | 130 mg/dL | 130 mg/dL (10 yr risk 10–20%) 160 mg/dL (10-yr risk < 10%) |
| 0–1 Risk Factor | <160 mg/dL | 160 mg/dL | 190 mg/dL |

The invention utilizes the health care management system described in WO 01/41037A3 to study data from patient populations for cardiovascular risk factors especially those factors related to LDL and HDL subclass. WO 01/41037AC is incorporated herein in its entirety. The text, Heart Disease Breakthrough, by Thomas Yannios, M. D. John Wiley & Son, Inc., New York, 1999 discusses management of heart disease and the role of HDL and LDL subclasses and is incorporated herein by reference.

SUMMARY OF THE INVENTION

In analyzing LDL and HDL subclass data from more than 65,000 cardiovascular patients, it has been found that indicia for patient treatment can be derived from LDL and HDL subclass information that is not available from NCEP risk factor data. Thus, the invention permits the identification of patients with healthy low density lipoprotein concentration (LDLC) and high density lipoprotein concentration (HDLC) levels who have an undesirable small dense LDL trait and deficient reverse cholesterol transport system. For example, it has unexpectedly been found that the determination of LDL III a +b permits the identification of patients who are in need of therapeutic lifestyle changes and drug therapy which are not evident from NCEP guidelines based on a conventional panel of lipid assays. Similarly HDL 2b values can be used to identify patients in need of lifestyle change or drug therapy. LDL III a+b and HDL 2b values combined is a powerful tool for identifying patients who need treatment which NCEP data indicate are not in need of treatment.

More particularly, it has been determined that cardiovascular patients with LDL III a+b levels, small dense LDL particles, of about 15% or more are in need of more aggressive cardiovascular healthcare management, i.e., lifestyle changes and drug therapy. This LDL III a+b measurement identifies about 40% of patients in need of treatment that are missed by only using NCEP guidelines. Thus, the NCEP guidelines for treatment which are based on the basic lipid panel described above are not capable of determining cardiovascular risk in a significant subpopulation of patients and result in not treating at risk cardiovascular patients.

The invention therefore encompasses a method for identifying patients with normal NCEP lipid levels who are in need of treatment for cardiovascular disease comprising measuring one or more LDL or HDL particle subtraction levels and identifying abnormal LDL or HDL subtraction levels.

LDL III a+b are the preferred LDL subclasses to be measured and HDL 2b is the preferred HDL subclass. Other factors such as lipoprotein (a) (Lp(a)), triglycerides, and homocysteine also provide highly useful information. LDL and HDL subclasses are determined by gradient gel electrophoresis (GGE), NMR, ultracentrifugation, or ion mobility analysis.

DETAILED DESCRIPTION OF THE INVENTION

Database Statistics:

There are 65,536 patients in the database of which 51% (33,463) have LDLC<130 mg/dL and 44% (20,149) have levels of LDLC<100 mg/dL. Furthermore, 47% (31,102) of all patients in the database have LDL IIIa+b measurements.

Methods:

Database search criteria was set at two LDL levels: patients with LDLC<130 and patients with LDLC<100.

Results:

Of the patients with LDLC<130 and measured LDL—by gradient gel electrophoresis (GGE), 74% had an LDL IIIa+b 15% (see below)—a value documented to raise cardiovascular risk by 3-fold.

A. LDLC<130 mg/dL=33,463 patients (51% of total volume)

1. LDLC<130 mg/dL with LDLIIIa+b 15%=74%
2. LDLC<130 mg/dL with LDLIIIa+b 20%=55%
3. Pheno A=19,653 or 44%
4. Pheno AB=5,568 or 17%
5. Pheno B=13,173 or 39%

**Note: Each database has a limiting population factor. The above search only uses two variables and the limiting factor is LDLIIIa+b (n=l 18,797). Each introduction of a new variable limits the population of the result.

Of the patients with LDLC<100 and measured LDL-GGE, 85% of them had a LDL IIIa+b 15%(see below).

B. LDLC<100 mg/dL=20,149 patients (44% of total volume)

1. LDLC<100 mg/dL with LDLIIIa+b 15%=85%
2. LDLC<100 mg/dL with LDLIIIa+b 20%=70%
3. Pheno A=8,411 or 42%
4. Pheno AB=3,431 or 17%
5. Pheno B=8,307 or 41%

In either case, patients considered to be under "control" and thought not to require further treatment by NCEP guidelines had a preponderance of small, dense atherogenic particles and required varying degrees of aggressive treatment.

Another aspect of the invention involves utilizing the HDL 2b subclass data in the database. If the LDLC<100 database is used, the invention provides a test for hard to treat or difficult patients. But, the LDL<100 database also illustrates that just driving down LDLC is not always the solution. On the other hand, the LDL<130 database may seem too conservative because the NCEP goal is 100 for patients with CHD or CHD risk equivalents, but it does adhere to the population of patients who have family history or haven't been treated and need to establish a baseline to monitor therapy. The four variable search of patients with LDLC<130, HDL>40, an LDL IIIa+b value, and/or an HDL 2b value exhibits similar results from the LDLC<130 database.

C. LDLC<130 mg/dL+HDLC>40 mg/dL=13,810
 1. (C) with LDLIIIa+b 15%=70%
 2. (C) with LDLIIIa+b 20%=43%
 3. (C) with HDL 2b>20%=56%
 4. (C) with LDLIIIa+b 15%+HDL 2b>20%=59%
 5. (C) with LDLIIIa+b 20%+HDL 2b >20%=40%

If it is assumed these patients have 2+risk factors, the LDLC<130 and HDL>40 are at "healthy" levels according to NCEP, but the same verdict is displayed as the above database search. 70% of the population has an elevated LDL IIIa+b. When HDL 2b is added to the equation, the percentage of patients with both abnormal LDL IIIa+b and HDL 2b values slightly lessen to 59%. Thus, about 6 out of 10 patients with "healthy" LDLC and HDLC levels express both the small dense LDL trait and deficient reverse cholesterol transport system.

The other four variable search of patients with LDLC<100, HDL>40, an LDL IIIa+b value, and/or an HDL 2b value exhibits similar results from its database sibling. The concomitant risk factors of elevated LDLIIIa+b and deficient HDL 2b occur 91% of the time.

D. LDLC<100 mg/dL+HDLC>40 mg/dL=11,334
 1. (D) with LDLIIIa+b 15%=84%
 2. (D) with LDLIIIa+b 20%=60%
 3. (D) with HDL 2b>20%=53%
 4. (D) with LDLIIIa+b 15%+HDL 2b>20%=91%
 5. (D) with LDLIIIa+b 20%+HDL 2b>20%=68%

Physicians who have patients with an LDLC value under control (<100) often conclude that they need no further information for treating the patient. This is not the case (See B), 85% of the population with LDL IIIa+b values were elevated and were in need of treatment.

There are several other aspects of the invention derived from the database analysis such as 61% of patients with LDL<100 or LDL<130 and TG<150 still have deficient or abnormal HDL 2b values (LDLC under control and triglyceride metabolism working fine, but unapparent deficient reverse cholesterol transport). All of these newly discovered relationships are summarized below in their respective database (LDLC<130 or LDLC<100).

Database Informatics (LDL<130 mg/dL)
(Total Database Volume: 65,536)
(Total of patients with LDL IIIa+b values: 31,102 (47%))
A. LDLC<130 mg/dL=33,463 patients (73% of total volume)
 1. LDLC<130 mg/dL with LDLIIIa+b 15%=74%
 2. LDLC<130 mg/dL with LDLIIIa+b 20%=55%
  a. Pheno A=19,653 or 43%
  b. Pheno AB=5,568 or 17%
  c. Pheno B=13,173 or 39%
B. LDLC<130 mg/dL+HDLC>40 mg/dL=13,810
 1. (B) with LDLIIIa+b 15%=70%
 2. (B) with LDLIIIa+b 20%=43%
 3. (B) with HDL 2b>20%=56%
 4. (B) with LDLIIIa+b 15%+HDL 2b>20%=59%
 5. (B) with LDLIIIa+b 20%+HDL 2b>20%=40%
C. LDLC<130 mg/dL+HDL2b<20%=13,168
 1.(C) with LDLIIIa+b 15%=86%
 2.(C) with LDLIIIa+b 20%=68%
D. LDLC<130 mg/dL+HDL2b>20%=3,642
 1. (D) with LDLIIIa+b 15%=77%
 2. (D) with LDLIIIa+b 20%=38%
E. LDLC<130 mg/dL+HDL2b>20%+Lp(a)>20 mg/dL=1,417
 1. (E) with LDLIIIa+b 15%=77%
 2. (E) with LDLIIIa+b 20%=38%
F. LDLC<130 mg/dL+Lp(a)>20 mg/dL=10,587
 1. (F) with LDLIIIa+b 15%=73%
 2. (F) with LDLIIIa+b 20%=52%
G. LDLC<130 mg/dL+HDLC>40 mg/dL=11,226
 1. (G) with LDLIIIa+b 15%=70%
 2. (G) with LDLIIIa+b 20%=43%
H. LDLC<130 mg/dL+TG<150 mg/dL=28,270
 1. (H) with LDLIIIa+b 15%=70%
 2. (H) with LDLIIIa+b 20%=42%
 3. (H) with HDL 2b<20%=62%
I. LDLC<130 mg/dL+TG<180 mg/dL=24,796
 1. (L) with LDLIIIa+b 15%=72%
 2. (L) with LDLIIIa+b 20%=46%
J. LDLC<130 mg/dL+TG<180 mg/dL+HDL>40 mg/dL=16,723
 1.(J) with LDLIIIa+b 15%=70%
 2.(J) with LDLIIIa+b 20%=30%
K. LDLC<130 mg/dL+TG<180 mg/dL+HDL2b>20%=3,549
 1. (K) with LDLIIIa+b 15%=68%
 2. (K) with LDLIIIa+b 20%=37%

Database Informatics (LDLC<100 mg/dL)
(Total Database Volume: 65,536)
(Total of patients with LDL IIIa+b values: 31,102 (47%))
A. LDLC<100 mg/dL=20,149 patients (44% of total volume)
 1.LDLC<100 mg/dL with LDLIIIa+b 15%=85%
 2.LDLC<100 mg/dL with LDLIIIa+b 20%=70%
  a. Pheno A=8,411 or 42%
  b. Pheno AB=3,431 or 17%
  c. Pheno B=8,307 or 41%
B. LDLC<100 mg/dL+HDLC>40 mg/dL=11,334
 1. (B) with LDLIIIa+b 15%=84%
 2. (B) with LDLIIIa+b 20%=60%
 3. (B) with HDL 2b>20%=53%
 4. (B) with LDLIIIa+b 15%+HDL 2b>20%=91%
 5. (B) with LDLIIIa+b 20%+HDL 2b >20%=68%
C. LDLC<100 mg/dL+HDL2b>20%=2,772
 1. (C) with LDLIIIa+b 15%=88%
 2. (C) with LDLIIIa+b 20%=58%
D. LDLC<100 mg/dL+HDL2b<20%=5,906
 1.(D) with LDLIIIa+b 15%=94%
 2.(D) with LDLIIIa+b 20%=81%

E. LDLC<100 mg/dL+HDL2b>20%+Lp(a)>20 mg/dL=901
   1.(E) with LDLIIIa+b 15%=92%
   2.(E) with LDLIIIa+b 20%=63%
F. LDLC<100 mg/dL+Lp(a)>20 mg/dL=6,024
   1.(F) with LDLIIIa+b 15%=86%
   2.(F) with LDLIIIa+b 20%=70%
G. LDLC<100 mg/dL+TG <180 mg/dL=14,414
   1.(G) with LDLIIIa+b 15%=84%
   2.(G) with LDLIIIa+b 20%=62%
H. LDLC<100 mg/dL+TG<150 mg/dL=12,513
   1.(H) with LDLIIIa+b 15%=84%
   2.(H) with LDLIIIa+b 20%=60%
   3.(I) with HDL 2b<20%=61%
I. LDLC<100 mg/dL+TG<150 mg/dL+Lp(a)>20 mg/dL=4117
   1.(I) with LDLIIIa+b 15%=85%
   2.(I) with LDLIIIa+b 20%=61%

The above examples illustrate the present invention and are not intended to limit it in spirit or scope.

What is claimed is:

1. A method for identifying patients with normal National Cholesterol Education Program (NCEP) lipid levels who are in need of treatment for cardiovascular disease comprising identifying those patients with LDL IIIa+b particle level above 15% of the total LDL particles "wherein the LDL IIIa+b particle levels are those determined by gradient gel electrophoresis".

2. A method for identifying patients with normal National Cholesterol Education Program (NCEP) lipid levels who are in need of treatment for cardiovascular disease comprising identifying patients where its level of HDL 2b particle is a level less than 20% of the total HDL particles "wherein the HDL 2b particle levels are those determined by gradient gel electrophoresis".

3. A method for identifying a human subject in need of cardiovascular disease treatment comprising identifying subjects having LDL III a+b levels of about 15% or more of the total LDL particles.

4. The method according to claim 1 wherein the human subject has an LDLC<130 mg/dl.

5. The method according to claim 2, wherein the human subject has an LDLC<130 mg/dl.

6. The method according to claim 3 wherein the human subject has HDL 2b <patients less than 20% of total HDL particles.

7. The method of claim 1 wherein the LDL and HDL subclass are determined by linear gel electrophoresis, segmented gradient gel electrophoresis, ultracentrifuge, or ion mobility analysis.

8. The method of claim 1 wherein the LDL and HDL subclass are measured by segmented gradient gel electrophoresis.

9. A method for identifying patients in need of treatment for cardiovascular disease who have and LDL of>thru 130 mg/DL comprising identifying those patients having LDL III a+b level above 15% of the total LDL particles and HDL 2b less than 20% of the total HDL particles "wherein the HDL 2b and LDL IIIa+b particle levels are those determined by gradient gel electrophoresis".

* * * * *

UNITED STATES PATENT AND TRADEMARK OFFICE
CERTIFICATE OF CORRECTION

PATENT NO. : 6,812,033 B2
DATED : November 2, 2004
INVENTOR(S) : David Shewmake, Frank Ruderman and Christopher Boggess It is certified that error appears in the above-identified patent and that said Letters Patent is hereby corrected as shown below:

Title page,
Item [54], Title, insert -- AT -- between "IDENTIFYING" and "RISK".

Column 2,
Lines 40, 45, 46, 57, 59 and 60, insert -- $\geq$ -- after "LDL IIIa+b".

Column 3,
Lines 19, 20, 22, 23, 40, 41, 43, 44, 62 and 63, insert -- $\geq$ -- after "LDL IIIa+b".

Column 4,
Lines 2, 3, 5, 6, 8, 9, 11, 12, 15, 16, 18 and 19, insert -- $\geq$ -- after "LDL IIIa+b";
Lines 21, 22, 24, 25, 28, 29, 32, 33, 36, 37 and 43, insert -- $\geq$ -- after "LDL IIIa+b";
Lines 44, 49, 50, 52, 53, 55, 56, 58 and 59, insert -- $\geq$ -- after "LDL IIIa+b".

Signed and Sealed this

Sixteenth Day of August, 2005

JON W. DUDAS
*Director of the United States Patent and Trademark Office*